(12) United States Patent
Schumacher et al.

(10) Patent No.: US 6,463,787 B1
(45) Date of Patent: Oct. 15, 2002

(54) MOUNTING FOR A QUARTZ CRYSTAL

(75) Inventors: Rolf Schumacher, Berlin; Mathias Wünsche, Zepernick, both of (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 09/528,935

(22) Filed: Mar. 20, 2000

(30) Foreign Application Priority Data

Mar. 23, 1999 (DE) .......................................... 199 14 109

(51) Int. Cl.⁷ .............................................. H01L 41/08
(52) U.S. Cl. ........................ 73/24.06; 73/31.06; 73/651; 310/355; 310/352
(58) Field of Search ................................. 310/319, 328, 310/329, 355, 345, 352; 73/19.03, 24.06, 31.06, 32 A, 35.11, 54.38, 54.41, 61.49, 61.61, 61.75, 61.79, 651

(56) References Cited

U.S. PATENT DOCUMENTS

| | | | |
|---|---|---|---|
| 3,746,898 A | * 7/1973 | Austin et al. | 310/9.4 |
| 4,393,688 A | * 7/1983 | Johnston et al. | 310/329 |
| 4,561,286 A | 12/1985 | Secker et al. | 73/24.06 |
| 4,917,499 A | 4/1990 | Champetier et al. | 374/14 |
| 5,189,332 A | * 2/1993 | Wild | 310/345 |
| 5,201,215 A | 4/1993 | Granstaff et al. | 73/54.41 |
| 5,250,870 A | * 10/1993 | Fenlon et al. | 310/345 |
| 5,895,840 A | * 4/1999 | Ohuchi et al. | 310/329 |
| 5,929,553 A | * 7/1999 | Suzuki et al. | 310/355 |
| 6,163,505 A | * 12/2000 | Meier et al. | 367/165 |

OTHER PUBLICATIONS

Angewandte Chemie "A Journal of the Gesellschaft Deutscher Chemiker", International Edition in English, vol. 29, No. 4, Apr. 1990, pp. 329–438.

* cited by examiner

*Primary Examiner*—Hezron Williams
*Assistant Examiner*—Rose M. Miller
(74) *Attorney, Agent, or Firm*—Paul & Paul

(57) ABSTRACT

In order to achieve reproducible vibration excitation of a quartz crystal even under the technical conditions which prevail when it is used for monitoring electroplating baths, a mounting for the quartz crystal 7 is proposed. The mounting for the quartz crystal 7 has two holding elements 3, 6, 14 detachably connected to one another as a form-fit, and at least two contact elements 5, 9 on the holding elements 3, 6, 14 brought into electrical contact with the contacting surfaces 32 of the quartz crystal 7. The quartz crystal 7 is fitted with the holding elements 3, 6, 14 and/or the contact elements 5, 9 at least one of the contact elements 9 being configured as a resilient body. The at least one resilient contact element 9 has an end face 34, 134 for electrically contacting the quartz crystal 7, the size of which face corresponds roughly to the size of the quartz crystal 7.

11 Claims, 4 Drawing Sheets

MOUNTING FOR A QUARTZ CRYSTAL

Figure 1:
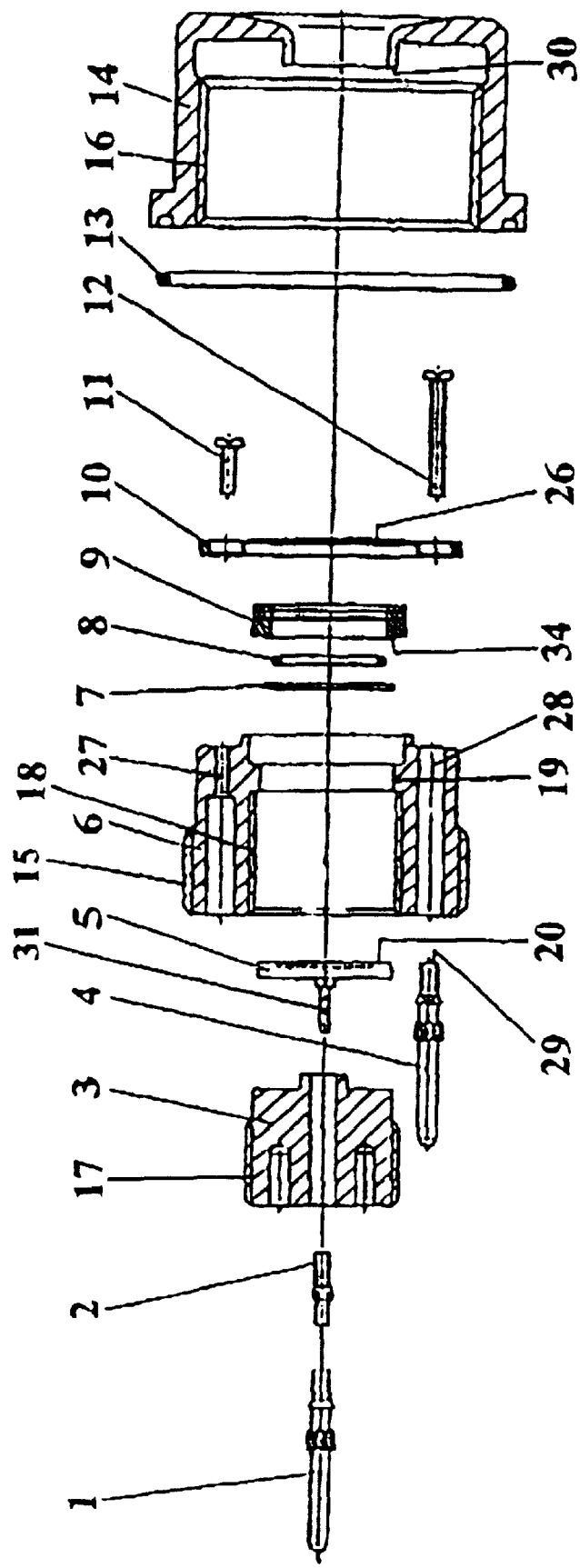

The invention relates to a mounting for a quartz crystal, which is configured as a disc and has metal layers on both sides as electrical contacting surfaces, and to a quartz crystal microbalance which includes such a mounting and a plug-in module adapted thereto.

The sensitive detection of alterations in mass with the aid of quartz crystal microbalances has been used successfully for several years already. For example such a measuring technique is used in the application of methods of surface coating, for example in the vapour deposition of metals or metal oxides. The method is based on the knowledge that a mass applied to a quartz crystal oscillating at its own natural frequency causes an easily measurable alteration in the oscillation frequency of the quartz with the frequency shift, alterations in mass which correspond to only a few atomic positions of the applied material can easily be detected. According to the quartz crystal used, the natural frequency of the quartz ranges from roughly 1 MHz to roughly 10 MHz. The frequency alteration which can here be identified, and which is in a large frequency range proportional to the amount of material applied, can be determined very exactly. The alteration in mass corresponding to the alteration in frequency can be calculated according to Sauerbrey's equation:

$$\Delta f = -[2 f_o{}^Q (A \sqrt{\mu_Q \rho_Q})^{-1} \Delta m]$$

here $f_o$ is the measurable frequency alteration on the basis of the alteration in mass $\Delta m$ of the quartz, $f_o$ is the natural frequency of the quartz without additional mass, A is the geometric electrode surface of the quartz, $\mu_o$ is the modulus of rigidity of the quartz and $\rho_o$ is the density of the quartz.

The principle of this measurement is based on the fact that the synthetic piezoelectric quartzes used when electrically excited in the megahertz range carry out a shear vibration. The vibration frequency depends on the thickness of the quartz and on the additional mass applied to the quartz, for example a vapour-deposited metal layer.

For roughly 35 years, the measurement of the alteration in mass $\Delta m$ with the quartz crystal microbalance has been used not only with coating methods in vacuum but also in electrochemical experiments in which one side of the quartz crystal is in complete contact with a liquid "The Quartz crystal microbalance: A Novel Approach to the In-Situ Investigation of Interfacial Phenomena at the Solid/Liquid Junction" by R. Schumacher in Angew. Chemie, Int. Ed., volume 29 (1990), pages 329 to 438). In this application, up to now predominantly scientific questions have been in the forefront, which arise during the investigation of interfacial reactions in liquid media. Together with further investigation methods, for example the measurement of the differential capacitance and the charge flow through the interface, this technique makes possible greater insight into interfacial reactions. For example this technique is sensitive enough also to detect the presence of absorbates on the quartz.

The quartz crystals are manufactured as thin wafers which are excited with an electronic oscillator circuit in shear vibrations parallel to the surface of the wafers. In order to transfer the excitation vibration to the quartz, contacting electrodes are applied to the quartz surfaces. For this purpose, large-area metal layers are for example vapour-deposited or sputtered onto both surfaces of the wafer, which layers are electrically connected to the exciting circuit. The oscillation frequency of the quartz is registered by means of standard measuring methods. For example in the essay by R. Schumacher, ibid., references are made to suitable oscillator circuits.

In U.S. Pat. No. 4,561,286 is described a piezoelectric contamination detector which is used in a gaseous environment. A quartz crystal is used in the detector. The quartz crystal is contacted via contact springs which are in contact with the contacting surfaces on the quartz.

In U.S. Pat. No. 4,917,499 is also described a device for analysing contamination in a gaseous environment, in which device the quartz crystal used is contacted electrically via springs. In this publication it is mentioned that these springs are used in order to achieve even distribution of the forces acting on the quartz, and thus to avoid the formation of tensions in the quartz.

In contrast to applications in which the quartz crystals are used in a gaseous environment, specific problems arise when quartz crystals are used which are in contact with liquid: on the one hand, care must be taken that no liquid reaches the electrical leads to) the contacting electrodes on the quartz and certainly does not come into contact with the electronic exciting circuit. Simultaneously, however, it must also be guaranteed that the excitation of the quartz vibrations is not hindered by the mounting of the quartz (R. Schumacher, ibid.). Simultaneously satisfying these two requirements is frequently difficult, since expediently mountings are used in which the quartz is not glued in, but in which the liquid-tightness is intended to be achieved by means of easily fitted and detachable sealing means, for example toroidal sealing rings to seal against penetrating fluid. The quartz is mechanically fixed with these sealing means so that the oscillation can be prevented.

In U.S. Pat. No. 5,201,215 is described a quartz crystal microbalance, in which the quartz crystal is in contact with a liquid and is contacted via securely connected contacts.

What has proved to be problematic is that the ability of the quartzes to start vibrating in a liquid is much lower than when used in a gaseous environment or in vacuum. In the latter case, on the other hand, the quartzes can be easily excited. If the quartzes are dipped into a liquid, the latter acts like a brake and dampens the shear vibration. The measures taken to prevent liquid from penetrating into the interior of the measurement cell in addition prevent the excitation of the quartz, such that the quartz vibration can altogether become easily unstable.

In particular in the monitoring of electroplating baths, metal s constantly deposited on the quartz crystal such that the deposited metal has to be removed intermittently again and again from the quartz. During the quick dissolution process desired for this purpose, the vibration excitation regularly breaks down, such that the vibration excitation has to be started up again once the dissolution process is completed. After several cycles of these deposition and subsequent dissolution processes, the quartzes have to be regularly exchanged in order to apply fresh metal layer electrodes to both sides of the quartz for renewed contacting. During the renewed fitting of the quartz, notice must be taken both of the low mechanical stability of the quartz wafers, the liquid-tightness of the measuring apparatus against penetrating liquid and of the reproducible vibration excitation of the quartzes. From these points of view the previously available techniques for fitting the quartz wafers do not guarantee any problem-free exchange since at least some of the above-mentioned problems almost always arise.

The problem underlying the present invention, therefore, is to avoid the disadvantages of the previously known quartz crystal microbalances and especially to find a device with which reproducible vibration excitation of the quartz can be also guaranteed under the technical conditions which prevail when it is used for monitoring electroplating baths.

Above all it must also be ensured that the bath liquid does not penetrate into the device, that the quartz crystal is easily exchangeable and that, after a sufficiently long period of time during which metal is deposited on the contacting surfaces, it can be freed of deposited metal again without any problem by means of an electrolytic method.

This problem is solved by the mounting according to the invention and according to claim 1 and the quartz crystal microbalance according to claim 11. Preferred embodiments of the invention are quoted in the subordinate claims.

The device according to the invention serves as a mounting for a quartz crystal which s configured as a disc and has metal layers on both sides as electrical contacting surfaces. Essential components of this mounting are two holding elements which are detachably connected to one another as a form-fit. Moreover, at least two contact elements, brought into electrical contact with the contacting surfaces of the quartz crystal, are provided on the holding elements. The quartz crystal is fixed with the holding elements and/or the contact elements. At east one of the contact elements is designed as a resilient body. In order to solve the above-mentioned problems, the at least one resilient contact element has an end face for electrically contacting the quartz crystal, the size of which face corresponds roughly to the size of the quartz crystal.

Electrical leads are provided to the contact elements.

The mounting is used in particular in a quartz crystal microbalance which can be used in the sense described initially for scientific investigations of electro-chemical processes on interfaces and for monitoring coating processes, for example in electroplating methods, but also in vacuum-coating methods. The quartz crystal microbalance is formed by the mounting according to the invention, including the feature that at least one of the contact elements is designed as a resilient body, and by an additional plug-in module with which the mounting can be detachably connected. The plug-in module has an electronic oscillator circuit for exciting the quartz crystal with its natural frequency. In addition, electrical leads are provided to the contact elements from the oscillator circuit via plug contacts between the mounting and the plug-in module.

With the mounting according to the invention it is possible for the first time to fit quartz crystals in a mounting so as to be easily exchangeable, with the proviso that the quartz oscillations can be generated reproducibly, even after metal deposited on the quartz crystal has been removed again quickly in an anodic dissolution process, and even after such deposition and dissolution processes have been carried out several tries.

It is assumed that the problems observed with the known devices could be traced back to insufficiently good electrical contacting of the containing surfaces on the quartz crystal during the fitting of the quartz. By now using a resilient body as the contact element, which has an end face for electrically contacting the quartz crystal, this face being of a size which corresponds roughly to the size of the quartz crystal, a large-area electrical contact between the contacting surfaces on the quartz crystal and the contact elements can be reproducibly produced. Even when minimal inaccuracies occur during the fitting of the quartz crystal which lead to tilting of the contact elements in relation to the contacting surfaces on the quartz, secure support of the contact elements on the contacting surfaces of the quartz crystal is guaranteed. Through the arrangement according to he invention, a form-fit detachable connection of the holding elements can also be selected instead of, for example, a glue connection, since obviously inaccuracies in fixing the quartz do not lead to a worsening of the electrical contacting. This is based probably on the fact that the resilient contact element can compensate for tolerances.

By a plug-in module being used for the quartz crystal microbalance, with which module the mounting can be detachably connected, what can furthermore be achieved is that the quartz crystals can be quickly exchanged in a problem-free manner, if a quartz crystal is no longer usable after repeated deposition and dissolution processes. Thus the increased assembly outlay For a quartz crystal during a process of exchanging the quartz in the quartz crystal microbalance for another does not have to be afforded. In the chosen conception, the plug contact includes the electronic circuit required for the vibration excitation of one quartz. Thus when the quartz is changed the circuit does not also have to be exchanged; therefore only one electronic circuit is required. As a result of the low spatial distance between the quartz crystal and the exciting circuit in the plug-in module, the oscillation stimulation behaviour is further improved.

The resilient body is preferably designed as a spring with end faces which are parallel to one another and serve the electrical contacting of the quartz crystal. This spring can include at least one central and two outer rings and/or discs arranged in stacks, respectively two rings and/or discs being connected to one another via at least one web, and the webs between two rings and/or discs being offset in relation to webs between adjacent rings and/or discs.

In a particularly preferred embodiment, the spring has a central and two outer rings and/or discs, arranged in stacks, respectively two rings and/or discs being connected to one another via two webs facing one another, and the two webs between the central and the one outer ring and/or the disc being arranged offset in relation to the two webs between the central and the other outer ring and/or the disc by respectively roughly 90°.

With this design of the resilient body, an extensive balancing of the tilting forces at the spring is achieved. With conventional springs, in contrast to this there is the disadvantageous tendency that tilting forces are not uniformly large in all directions. This means that secure support of the end faces of the contact elements on the contacting surfaces of the quartz crystal can no longer be easily guaranteed.

The balancing of tilting forces acting on the end faces of the spring is achieved all the more, the more webs are provided between two rings and/or discs. However, the spring constant is also greater as the number of webs increases, such that there is an optimum of two webs between two rings and/or discs.

In an alternative embodiment, the spring can include at least two rings and/or discs arranged in stacks and which are respectively connected to one another by at least two webs, all the webs between two rings and/or discs forming an equal angle of between roughly 10° and roughly 80° to the spring axis. By setting an angle of between roughly 10° and roughly 80° between the webs and the spring axis, and through the choice of the material and the material thickness of the webs, the spring constant is adjusted. With this structure, too, an extensive balancing of the spring against tilting forces is achieved.

In a further embodiment, the resilient body can also be designed as a hydraulic element with end faces which are parallel to one another and which serve the electrical contacting of the quartz crystal. For example, the element could be designed as a hollow toroidal sealing ring, which is filled with gas or liquid and which is disposed between two rings and/or discs with the end faces serving the contacting. Alternatively, the resilient contact element could also include two discs, of which one has a cavity filled with gas or liquid, in which precision bores distributed evenly over the disc surface are introduced with dies fitted therein. The second disc rests in this case against the hydraulically moveable die.

For easy and quick fixing of the quartz crystal, the mounting is so realised that the holding elements are screwed to one another or are connected to one another by a bayonet lock. To exchange the quartz, in this case the holding elements are merely screwed away from one another or the bayonet lock is released, the old quartz crystal is taken from the device, and after a new quartz has been fitted, the holding elements are screwed to one another again or the bayonet lock is closed. Furthermore, the holding elements can also be connected to one another by means of a snap closure.

To use the mounting in a quartz crystal microbalance, one side of the quartz crystal comes into contact with the fluid medium located outside the mounting, (gas or liquid). For this purpose, the one contact element is configured disc-shaped (for the rear side contacting) and the other contact element is configured annular (for the front side contacting), the contact elements being equipped respectively with metallic end faces which stand perpendicular to the axis of the screw connection or of the bayonet lock and which serve the electrical contacting of the quartz crystal. The end face of the annular contact element is naturally also annular, such that the fluid medium in the region inside the annular opening at the end face can reach the one side of the quartz crystal.

For simple and reliable contacting of the two quartz contacting surfaces, in this case both contact elements are detachably connected to one of the holding elements. So that the fluid medium can come into contact with the one side of the quartz crystal, the holding element with which the contact elements are not connected is configured annular. The annular contact element is fitted to the side of the quartz crystal facing the annular holding element, such that fluid medium located outside the mounting can come into contact with the one side of the fixed quartz crystal.

Figure 2:
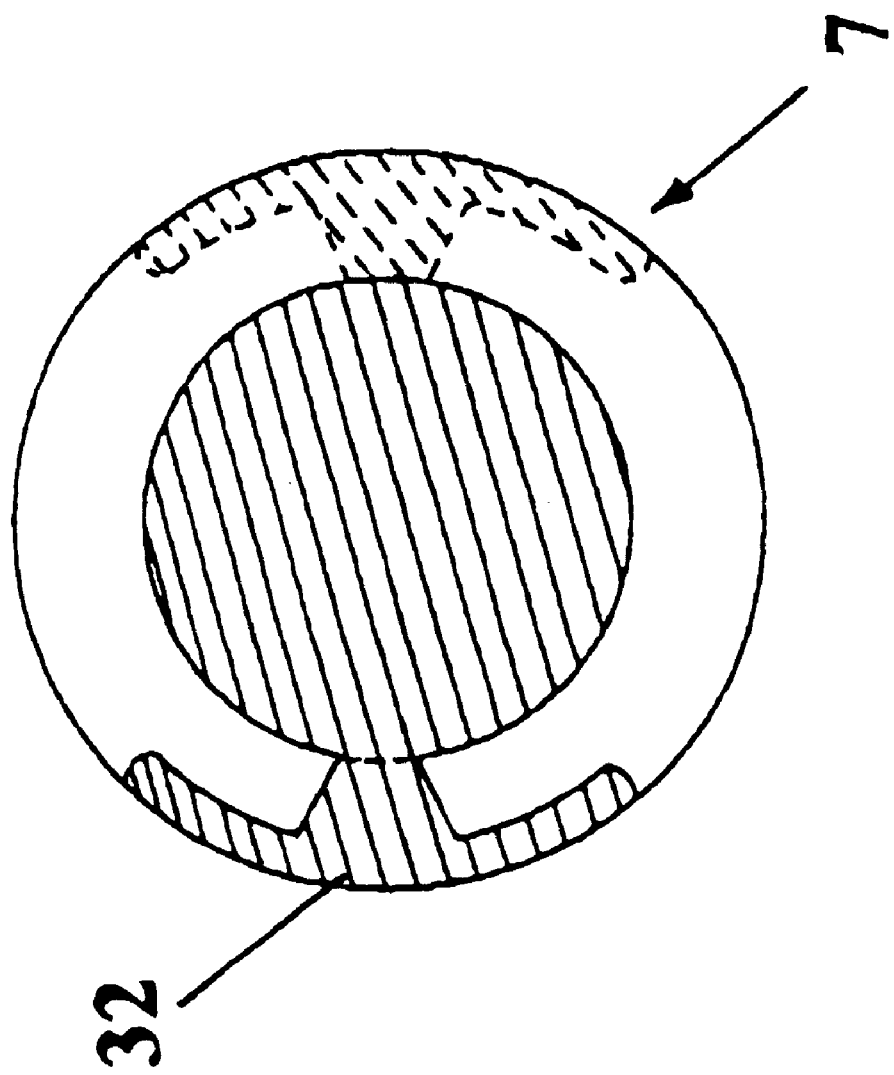
Figure 3:
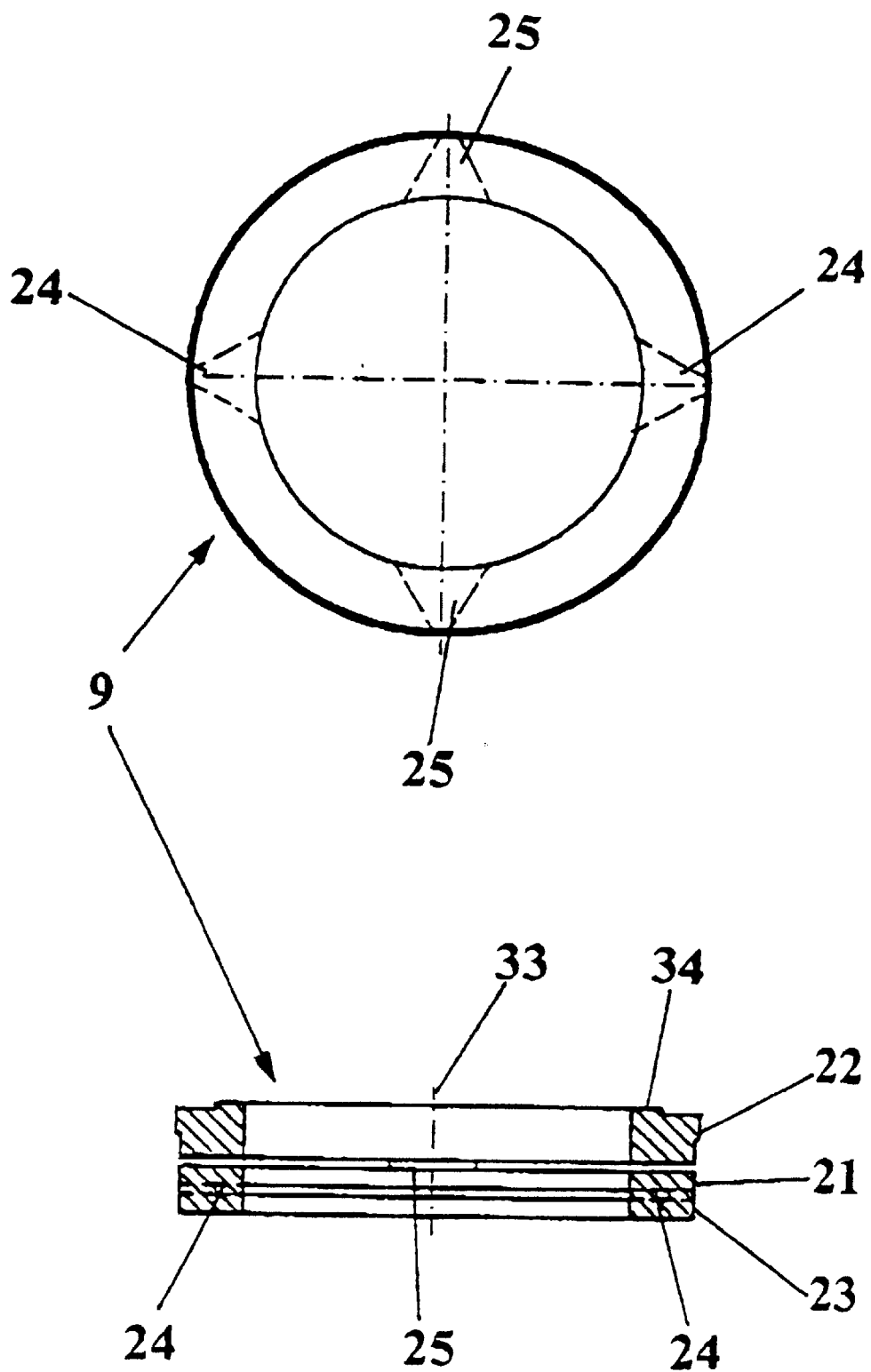
Figure 4:
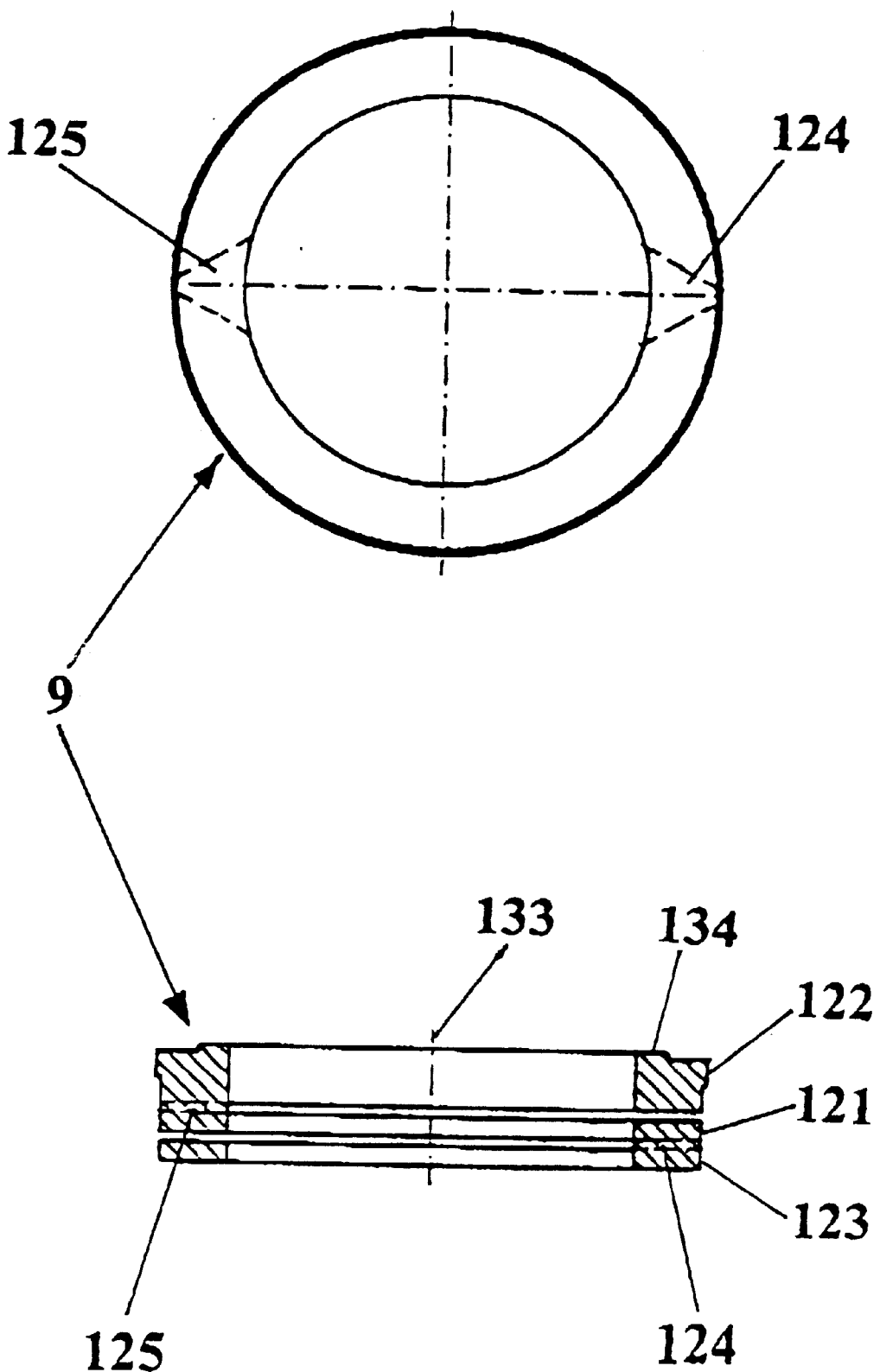

Reference is made to FIGS. 1 to 4 for the following explanation of the invention. The figures show:

FIG. 1: an exploded view of the mounting, in side view;

FIG. 2: plan view of a quartz crystal;

FIG. 3: plan view and section of a spring in a first embodiment;

FIG. 4: plan view and section of a spring in a second embodiment.

Represented in FIG. 1 are the individual components of a mounting according to the invention. The one holding element, consisting of a carcass 6 and the end piece 3, and the other holding element 14 are realised as parts which may be screwed to one another. The threads in the two holding elements are referred to by the reference numbers 15 and 16.

The carcass 6 is also able to be screwed to the end piece 3. The threads in parts 3 and 6 are referred to by the reference numbers 17 and 18.

In the inner region of carcass 6 is provided a projection 19 on which the contact element 5 can lie. This contact element consists of metal, for example brass, and is configured as a disc with contact surface 20. Contact element 5 is fixed by screwing end piece 3 into carcass 6.

The quartz crystal 7 is inserted into the carcass 6 from the right-hand side in FIG. 1. Through projection 19 a clear opening is formed in which the quartz. crystal 7 can be received.

From the right-hand side in FIG. 1, furthermore, the second contact element 9 is brought into contact with the quartz crystal 7. This contact element is not designed as a disc but as an annular part. According to the present invention, contact element 9 is resilient and can lie well on the quartz crystal surface to produce an optimal electrical contact to the quartz crystal 7.

The quartz crystal 7 has piezoelectric properties. Mechanical vibrations can be generated by applying an electric voltage to the quartz, e.g. where an electrical field modulated with high frequency in the MHz range is generated in the quartz. For this purpose, metallic electrodes are to be applied on the front and on the rear side of the quartz disc, for example by sputtering on. It has proved to be advantageous to first apply a thin chrome layer and thereafter a copper, nickel, platinum and/or gold layer. The layers have on the front and on the rear side the form shown in FIG. 2 (front side: area hatched and marked with continuous boundary lines; rear side: area marked with broken boundary lines)

From the rear side (in FIG. 1 from the left-hand side), the quartz crystal 7 is contacted with contact element 5 by the annular contact surface 20 of the contact disc of contact element 5 lying on the rear-side metal layer of the quartz crystal 7. From the front side, the metallic edge region 32 on the quartz 7 is contacted via the annular end face 34 of the resilient contact element 9 by this end face lying exclusively in the edge region of the quartz 7.

In this embodiment, the resilient contact element 9 is configured as a spring consisting of metal, for example brass. A preferred embodiment of this spring is shown in detail in FIG. 3 in a plan view (top) and in section (below). Contact element 9 is substantially constructed from three rings: a central ring 21 and two outer rings 22 and 23 which are arranged in stacks.

The rings are connected to one another via webs 24 between rings 21 and 23 and webs 25 between rings 21 and 22. Webs 24 lie opposite one another offset by 180°. The same is also true for webs 25. Webs 24 are offset in relation to webs 25 by 90°.

Through the special arrangement of webs 24, 25 extensive balancing of the tilting forces at the spring 9 is achieved, whose tendency to tilt towards the spring axis 33 is approximately the same in all directions. What is achieved thereby is that the end face 34 of ring 22 facing the quartz crystal 7 sits very close to the contacting surface 32 on the quartz crystal 7 and thus a very good electrical contact is produced. This result is also maintained even when, through insufficiently accurate production of the individual carts of the mounting, no exact plane parallel configuration of the components in respect of one another is possible and tolerances therefore have to be compensated for with the spring 9.

In an alternative embodiment (FIG. 4) only two webs are provided, namely a web 124 between rings 121 and 123 and a web 125 between rings 121 and 122.

The resilient contact element 9 is fixed in the desired position by a contact plate 10. This contact plate is also configured annular in order to render possible the admission of fluid medium to one side of the quartz crystal 7 (right-hand side in FIG. 1). The contact plate 10 has on the inner edge of the ring a bulge 26 which serves to fix the contact element 9 exactly at the desired point, in the carcass 6.

Contact plate 10 may be screwed to the carcass 6, in order to fix the quartz crystal 7 and the resilient contact element 9 in the desired position. This purpose is served by screws 11 and 12 which may be screwed into the associated bores 27, 28. To this end a threaded bore 27 is provided in carcass 6 for screw 11. An unthreaded bore 28 is provided for screw 12. Screw 12 is screwed to contact pin 4 which for this purpose has a thread 29 at one end.

To seal the carcass 6 and particularly the rear side of the quartz crystal 7 and the electrical leads against penetrating liquid, the additional holding element 14 is screwed onto the carcass 6. When fitted, holding element 14 lies with its lip 30 over a toroidal sealing ring 8 on the front side of the quartz crystal 7 and ensures in addition the fit of the latter.

To supply electrical impulses to the contact elements 5 and 9, contact pins 1 and 4 are provided which are fitted into corresponding plug connections in a plug-in module not shown here. In the present case, contact pin 1 is connected via an adapter piece 2 to pin 31 of the rear-side contact element 5.

The above-described mounting 5 secured via contact pins 1 and 4 with the plug-in module, in which an oscillator circuit is located to excite the quartz crystal. To seal the parting line between the mounting and the plug-in module against penetrating liquid, a toroidal sealing ring 13 is provided, by means of which a secure fit of the holding element 14 against the plug-in module is achieved. The plug-in module is secured with a suitable additional mounting in the bath container for the bath liquid to be examined or to the experimental test cell in known manner.

A standard circuit arrangement with an oscillating circuit (for example a Wien bridge oscillator with an amplitude control) may be used as the oscillator circuit.

LIST OF REFERENCE NUMBERS 1 contact pin
2 adapter piece for contact pin 1
3 end piece
4 contact pin
5 contact element
6 carcass
7 quartz crystal
8 toroidal sealing ring
9 resilient contact element, spring
10 contact plate
11 screw
12 screw
13 toroidal sealing ring
14 holding element
15 external thread on carcass 6
16 internal thread on holding element 14
17 external thread on end piece 3
18 internal thread on carcass 6
19 projection in carcass 6
20 contact surface on contact element 5
21, 121 central ring of spring 9
22, 122 outer ring of spring 9
23, 123 outer ring of spring 9
24, 124 webs between rings 21, 121 and 23, 123
25, 125 webs between rings 21, 121 and 22, 122
26 bulge on the contact plate 10
27 threaded bore in carcass 6
28 bore in carcass 6
29 thread in contact pin 4
30 lip on holding element 14
31 pin on contact element 5
32 front-side contacting surface on quartz crystal 7
33, 133 spring axis
34, 134 end face of contact element 9

What is claimed is:

1. Mounting for a quartz crystal which is configured as a disc and has metal layers on both sides as electrical contacting surfaces which mounting has holding elements detachably connected to one another as a form-fit and at least two contact elements on the holding elements, brought into electrical contact with the contacting surfaces of the quartz crystal, the quartz crystal being fixed with the holding elements and/or the contact elements and at least one of the contact elements being designed as a resilient body, characterised in that the at least one resilient contact element (9) has an end face (34, 134) for electrically contacting the quartz crystal (7), the size of which face is similar to the size or circumference of the quartz crystal.

2. Mounting according to claim 1, characterised in that the resilient body (9) is configured as a sprang with end faces (34, 135) which are parallel to one another and serve the electrical contacting of the quartz crystal (7).

3. Mounting according to claim 2, characterised in that the spring (9) includes at least one central (121) and two outer (122, 123) rings arranged in stacks, respectively two rings being connected to one another via at least one web (124, 125) and the webs (124) between two rings (121, 123) being offset in relation to webs (125) between adjacent rings (121, 122).

4. Mounting according to claim 2, characterised in that the spring (9) has a central (21) and two external (22, 23) rings arranged in stacks, respectively two rings being connected to one another via two webs (24, 25) lying opposite one another, and the two webs (24) between the central and the one outer ring (21, 23) being offset in relation to the two webs (25) between the central and the other outer ring (21, 22) by respectively roughly 90°.

5. Mounting according to claim 2, characterised in that the spring (9) includes at least two rings (21, 22, 23) arranged in stacks and which are respectively connected to one another by at least two webs (24, 25), all the webs between two rings forming an identical angle of between roughly 10° and roughly 80° C. to the spring axis.

6. Mounting according to claim 1, characterised in that the resilient body (9) is configured as a hydraulic element with end faces (34, 134) which are parallel to one another and serve the electrical contacting of the quartz crystal (7).

7. Mounting according to one of the preceding claims, characterised in that the holding elements (3, 6, 14) are screwed to one another or are connected to one another via a bayonet lock.

8. Mounting according to claim 7, characterised in that the one contact element is configured disc-shaped and the other contact element annular, both respectively having metallic end faces (20, 34, 134) which stand perpendicular on the axis of the screw connection or of the bayonet lock and serve the electrical contacting of the quartz crystal (7).

9. Mounting according to claim 8, characterised in that the two contact elements (5, 9) are detachably connected to one of the holding elements (3, 6), in that the other holding element (14) is configured annular, and in that the annular contact element is disposed on the side of the quartz crystal (7) facing the annular holding element, such that fluid located outside the mounting can be brought into contact with the one side of the fixed quartz crystal.

10. Mounting according to one of the preceding claims 1–6, characterised in that electrical leads (1, 2, 4, 10) are provided to the contact elements (5, 9).

11. Quartz crystal microbalance having a mounting for a quartz crystal which is configured as a disc and has metal layers on both sides as electrical contacting surfaces, which mounting has two holding elements detachably connected to one another as a form-fit and at least two contact elements on the holding elements brought into electrical contact with the contacting surfaces of the quartz crystal, the quartz crystal being fixed with the holding elements and/or the contact elements, and at least one of the contact elements being designed as a resilient body, and having a plug-in module, with which the mounting is detachably connected, with an electronic oscillator circuit to excite the quartz crystal with its natural frequency, wherein electrical leads are provided from the oscillator circuit to the contact elements via plug contacts between the mounting and the plug-in module, characterised in that the at least one resilient contact element (9) has an end face (34, 134) for electrically contacting the quartz crystal (7), the size of which face corresponds roughly to the size of the quartz crystal.

* * * * *